(12) United States Patent
Sudol et al.

(10) Patent No.: US 6,440,076 B1
(45) Date of Patent: Aug. 27, 2002

(54) ULTRASOUND TRANSDUCER CONNECTOR ASSEMBLY

(75) Inventors: Wojtek Sudol, North Andoer, MA (US); Francis E. Gurrie, North Andover, MA (US); Walter Patrick Kelly, Jr., Goffstown; David P Dolan, Londonderry, both of NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 35 days.

(21) Appl. No.: 09/711,055

(22) Filed: Nov. 9, 2000

(51) Int. Cl.$^7$ ............................................. A61B 08/00
(52) U.S. Cl. ...................................... 600/459; 600/460
(58) Field of Search ................................. 600/437, 449, 600/463, 461, 460, 432, 459; 118/916; 439/606

(56) References Cited

U.S. PATENT DOCUMENTS

| | | | |
|---|---|---|---|
| 5,150,715 A | * 9/1992 | Ishiguro et al. ............. 600/463 |
| 5,590,658 A | 1/1997 | Chiang et al. |
| 5,603,323 A | 2/1997 | Pflugrath et al. |
| 5,636,631 A | 6/1997 | Waitz et al. |
| 5,690,114 A | 11/1997 | Chiang et al. |
| 5,715,823 A | 2/1998 | Wood et al. |
| 5,722,412 A | 3/1998 | Pflugrath et al. |
| 5,817,024 A | 10/1998 | Ogle et al. |
| 5,839,442 A | 11/1998 | Chiang et al. |
| 5,851,186 A | 12/1998 | Wood et al. |
| 5,879,303 A | 3/1999 | Averkiou et al. |
| 5,891,035 A | 4/1999 | Wood et al. |
| 5,893,363 A | 4/1999 | Little et al. |
| 5,897,498 A | 4/1999 | Canfield et al. |
| 5,938,607 A | 8/1999 | Jago et al. |
| 5,957,727 A | * 9/1999 | Page, Jr. ..................... 439/607 |
| 5,957,846 A | 9/1999 | Chiang et al. |
| 5,964,709 A | 10/1999 | Chiang et al. |
| 5,997,479 A | 12/1999 | Savord et al. |
| 6,007,490 A | * 12/1999 | Pawluskiewicz ............ 600/459 |
| 6,013,032 A | 1/2000 | Savord |
| 6,102,860 A | * 8/2000 | Mooney ..................... 128/916 |
| 6,102,863 A | 8/2000 | Pflugrath et al. |
| 6,106,468 A | 8/2000 | Dowdell |
| 6,106,472 A | 8/2000 | Chiang et al. |
| 6,113,547 A | 9/2000 | Catallo et al. |
| 6,117,084 A | 9/2000 | Green et al. |
| 6,117,085 A | 9/2000 | Picatti et al. |
| 6,135,961 A | 10/2000 | Pflugrath et al. |
| 6,162,093 A | * 12/2000 | Sudol et al. ................ 439/606 |

OTHER PUBLICATIONS

Terason 2000 information obtained from url: www.terason.com/terason2000.htm; 6 pages.
Sonosite 180 information obtained from url: www.sonosite.com/products_180_heart.html; 5 pages.
SonoHeart Applications Summary obtained from the SonoSite brochure; 2 pages.

* cited by examiner

*Primary Examiner*—Francis J. Jaworski
*Assistant Examiner*—Maulin Patel
(74) *Attorney, Agent, or Firm*—John Vodopia

(57) ABSTRACT

An ultrasound transducer connector for connecting a transducer to a terminal on an ultrasound unit, the ultrasound transducer connector including a shell; a LIF connector supported by the shell; and a cable electrically connected to the LIF connector that electrically connects the LIF connector to the transducer.

15 Claims, 11 Drawing Sheets

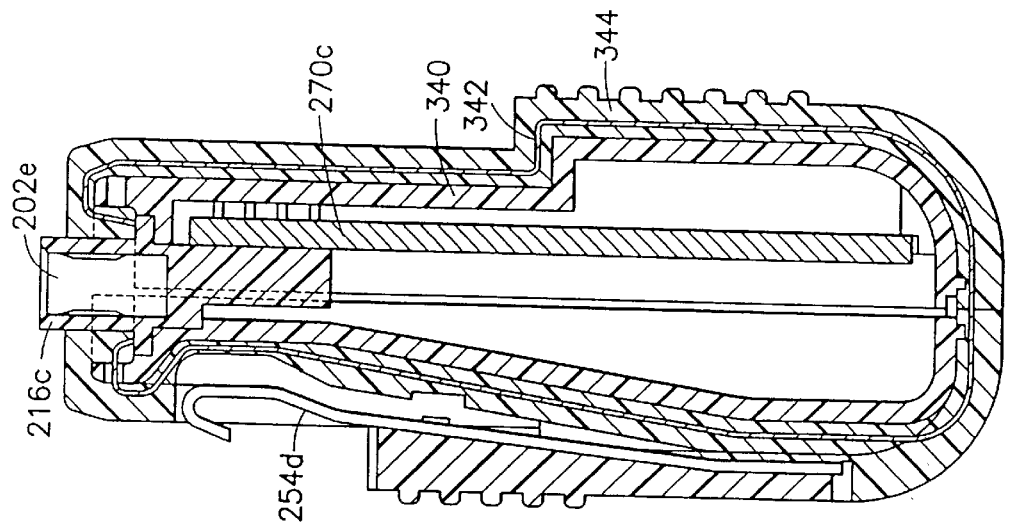
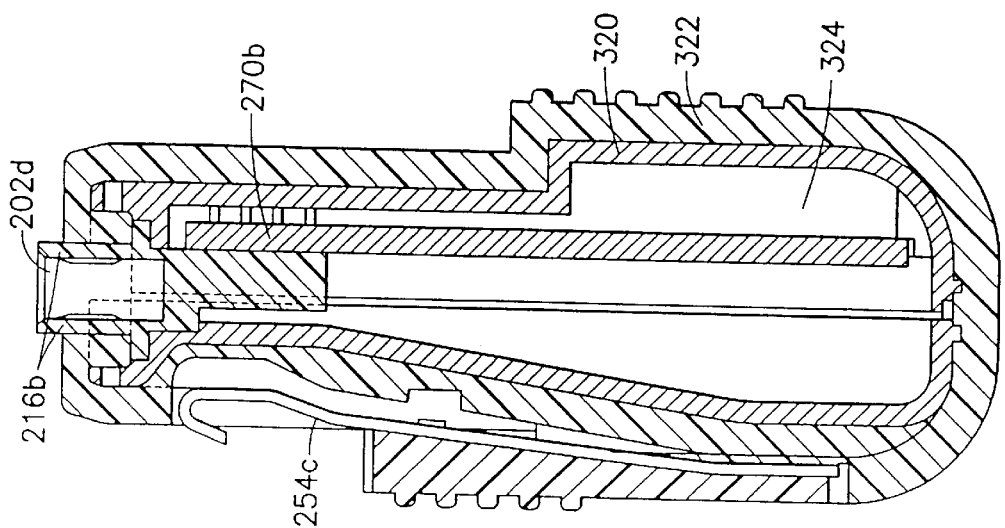

ULTRASOUND TRANSDUCER CONNECTOR ASSEMBLY

FIELD OF THE INVENTION

This invention relates to ultrasound transducer connector assemblies and, more particularly, to an ultrasound transducer connector assembly that includes a low insertion force connector, a leaf spring latch and several alternative housing configurations.

BACKGROUND OF THE INVENTION

FIG. 1. illustrates a typical ultrasound system 10. An ultrasound transducer 12 is coupled to its associated ultrasound console 14 via a cable 16, which is routed into an ultrasound transducer connector assembly 18, mates with a corresponding terminal 20 located on ultrasound console 14.

FIG. 2 offers a more detailed representation of ultrasound transducer connector assembly 18, and shows an electrical circuit 30 and an electrical connector 22 enclosed within a connector housing 24. Electrical connector 22 may have as many as 500 contacts (not shown). To protect the integrity of the electrical signals, a radio frequency interference (RFI) shield 26 is disposed about electrical circuit 30 and coupled to coaxial (coax) shield 28. In the prior art, electrical connector 22 is a zero insertion force (ZIF) connector.

FIG. 3 illustrates a generic ZIF connector 110. It includes a movable connector component 112 with movable electrical contacts 114, designed to mate with a stationary connector component 116 having stationary electrical contacts 118.

For mating, movable connector component 116 is brought towards stationary connector component 116 in the direction indicated by arrow 120. Initially, there is a gap 122 separating movable electrical contact 114 from stationary electrical contact 118, so that the contacts are not subjected to any friction or insertion force. A locking mechanism 124 traverses movable connector component 112 through an aperture 126 and is received in a recess 128 of stationary connector component 116. Locking mechanism 124 is rotated, as indicated by arrow 130, causing movable connector component 112 to close in the direction of arrow 132. This reduces gap 122 allowing movable electrical contact 114 to wipe against stationary electrical contact 118 to make an electrical connection.

ZIF connectors minimize the physical stress exerted upon their electrical contacts, thus avoiding wear and potential damage to the contacts. However, these connectors are mechanically more complex, larger and more expensive than simpler connectors.

Although ZIF locking mechanism 124 offers some latching capability to help secure movable connector component 112 with stationary connector component 116, this latching alone is not sufficient to secure the mating of a typical ultrasound transducer connector assembly to its ultrasound console. Accordingly, ultrasound transducer connectors usually include a latching mechanism in addition to the incidental latching offered by the ZIF connector.

FIG. 4 illustrates a prior art ultrasound transducer connector assembly 150 with a ¼ turn latching mechanism comprising a handle 152 and a shaft 154. Shaft 154 traverses an outer shell 156, and has an end 158 that guides ultrasound transducer connector assembly 150 into a mating connector assembly (not shown). The connection is secured by rotating handle 152 to lock ultrasound transducer connector assembly 150 into its mate. The ¼ turn latching mechanism is mechanically more complex, larger and more expensive than simpler latching mechanisms.

RFI shielding is provided by some form of electrically conductive barrier disposed about the electrical circuit for which protection is desired. The prior art generally provides RFI shielding by enclosing the circuitry within a connector housing comprised of either a metal outer shell or a metal inner shell surrounded by a plastic outer shell. For example, referring again to FIG. 4, the prior art connector assembly 150 includes outer shell 156 made of metal.

When components such as these are manufactured, their physical dimensions must be held to fairly strict tolerances to ensure proper fit during assembly. Additionally, metal is generally more expensive than plastic. Therefore, the cost of an ultrasound transducer connector assembly can be reduced by minimizing the use of components with strict manufacturing tolerances, and by using plastic rather than metal where possible.

Accordingly, there is a need for an ultrasound transducer connector assembly with an electrical connector of minimal mechanical complexity, size and cost, and a latching mechanism of minimal mechanical complexity, size and cost. There is a further need for an ultrasound transducer connector assembly with an RFI shield and connector housing minimizing the use of components requiring strict manufacturing tolerances and minimizing the use of metal components.

SUMMARY OF THE INVENTION

The present invention is directed toward improvement of prior art ultrasound transducer connector assembly 18 (FIGS. 1 and 2).

The new ultrasound transducer connector assembly includes a low insertion force (LIF) connector rather then a ZIF connector as typically used in the prior art. A low insertion force connector requires an insertion force of 20–100 grams/contact to effectuate mating of the connector, and corresponding contacts actively wipe against one another during the act of insertion. The preferred embodiment uses a multi-row, plate-on-beam connector with contact spacing of less than 3mm. This preferred connector is mechanically less complex, smaller and less expensive than the ZIF connectors used in the prior art.

The new ultrasound transducer connector assembly includes a latch that is engaged/disengaged with a push movement rather than the turning movement as typically used in the prior art. Latches, such as a leaf spring latch, that engage/disengage with a push movement are mechanically less complex, significantly smaller and less expensive than latches that use a turning mechanism.

BRIEF DESCRIPTION OF THE DRAWINGS

FIG. 9 is a cross-sectional view of a new ultrasound transducer connector assembly employing a second housing configuration.

FIG. 10 is a cross-sectional view of a new ultrasound transducer connector assembly employing a third housing configuration.

DETAILED DESCRIPTION OF THE PREFERRED EMBODIMENTS

The new ultrasound transducer connector assembly comprises a low insertion force (LIF) connector, a latch mechanism, a cable strain relief and a housing. A LIF type connector insert facilitates a reduced transducer connector size.

In most transducer assemblies (including the probe, cable and connector) the connector must house a certain amount of electronics, for example: circuits for routing the signal form the connector insert to the cable; circuits for transducer timing; signal amplification; or other signal processing circuits. In current ZIF style connectors, these circuits are often integrated onto multiple printed circuits boards (PCBs), often referred to as modules. It is difficult and expensive to achieve further integration by reducing the number of PCBs to one (1) mostly due to the fact that ZIF connectors typically have a pitch of at least 2mm.

LIF connectors typically have a pitch of less than 1mm facilitating the integration of all the desired circuits onto a single PCB. This high level of integration has several advantages, such as reduced weight (for example less than 200 grams versus 300–500 grams for a ZIF connector), and reduced size and volume (less than or equal to 10 cubic inches)

Figure 1:
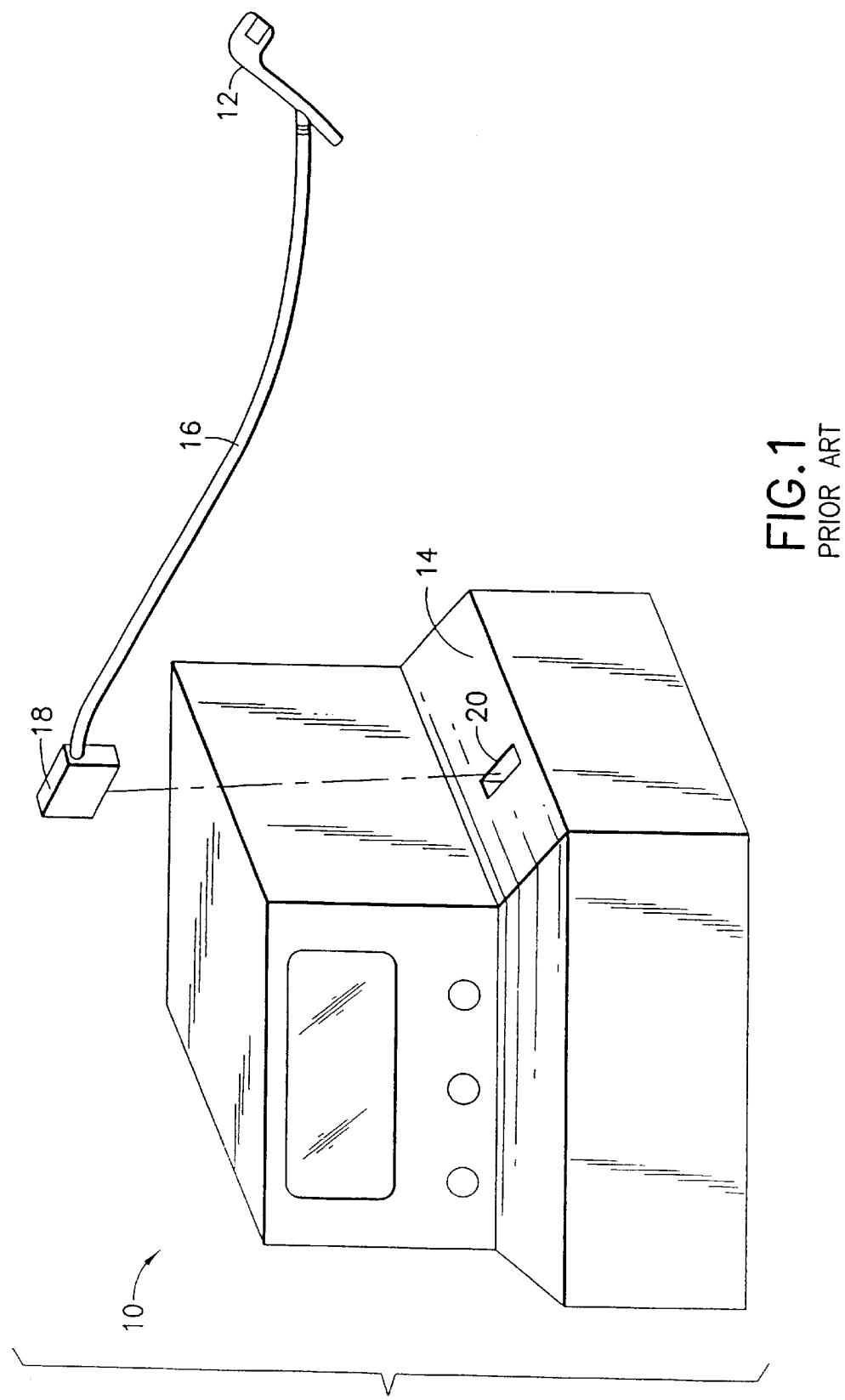
FIG. 1 is a diagram of a typical ultrasound system.
Figure 2:
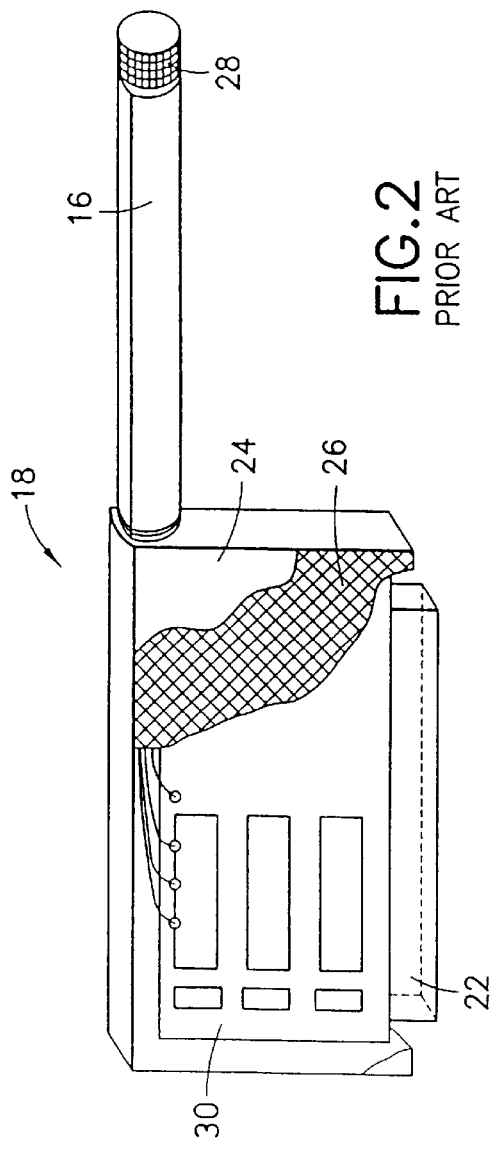
FIG. 2. is a front elevational view, with portions broken away, of a typical ultrasound transducer connector assembly.
Figure 5:
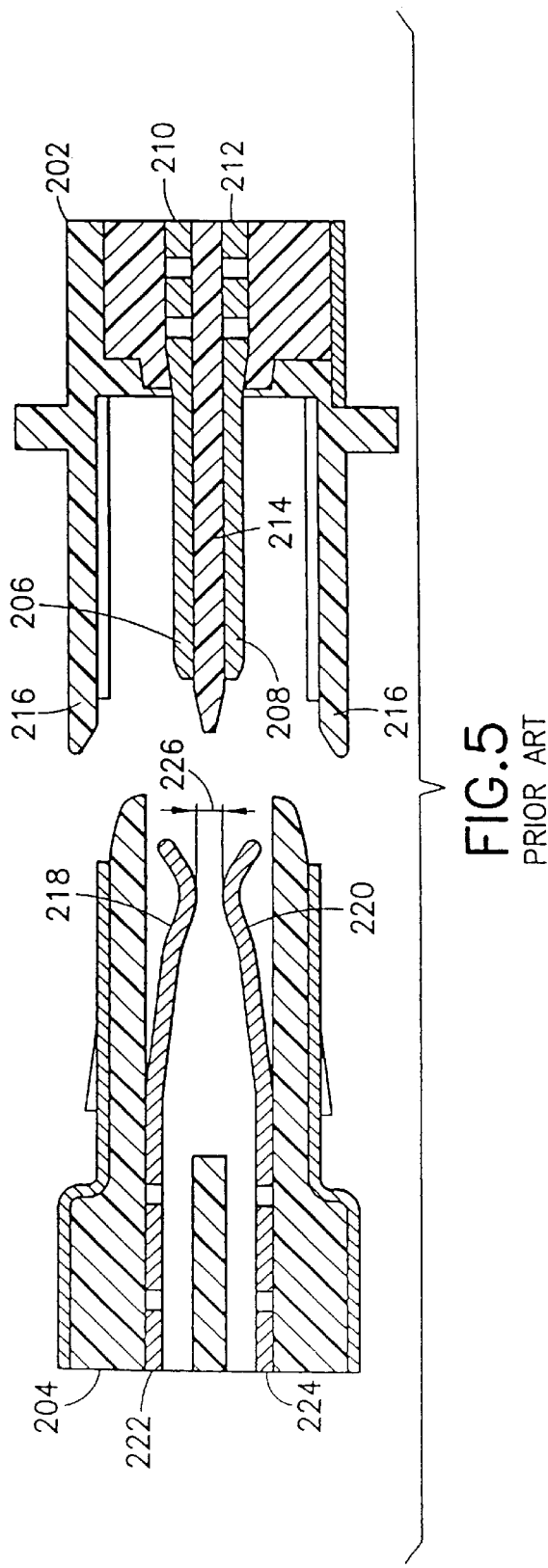
FIG. 5 is a cross-sectional view of a plate-on-beam connector.
Figure 3:
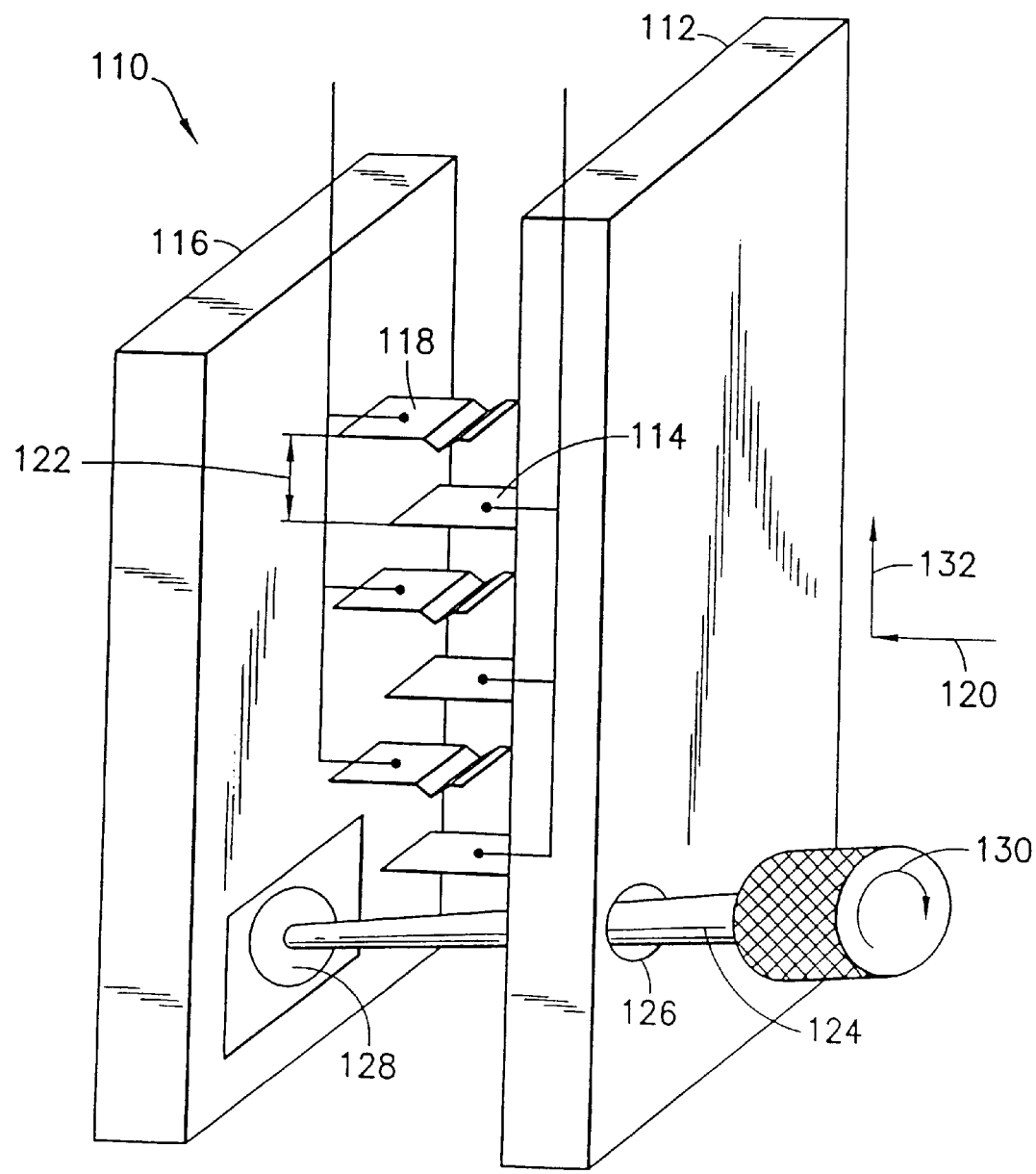
FIG. 3 is a diagram of a zero insertion force connector.
Figure 4:
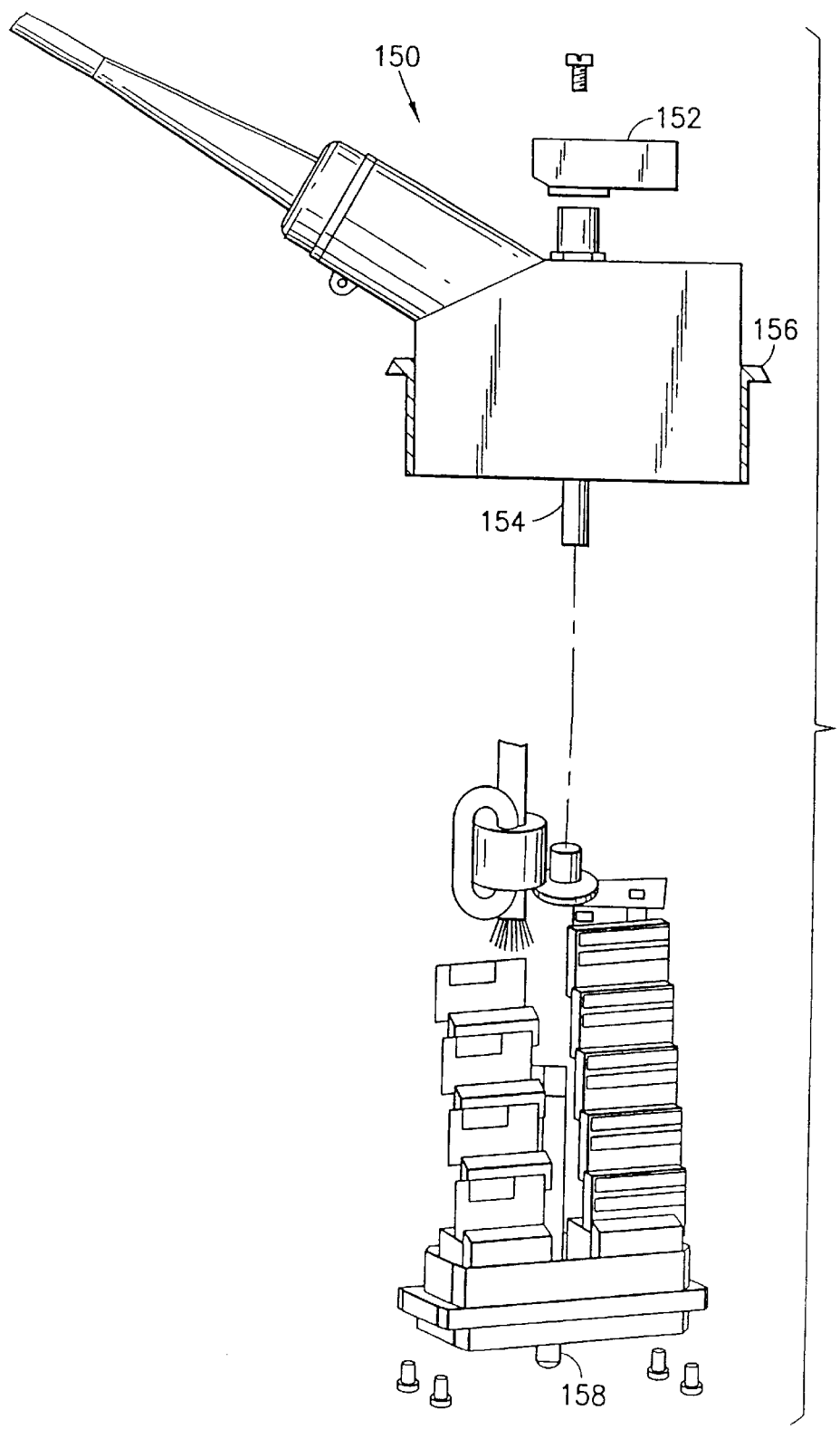
FIG. 4 is an exploded view of a prior art ultrasound transducer connector assembly.

FIG. 5. shows a low insertion force connector commonly known as a plate-on-beam connector. Plate-on-beam connector 200 includes a first LIF connector part 202 and a second LIF connector part 204.

First LIF connector part 202 has two electrically conductive surfaces, i.e., a plate A 206 and a plate B 208. Plate A 206 and plate B 208 can be electrically coupled to an electrical circuit (not shown) via a plate A terminal 210 and a plate B terminal 212, respectively. Plate A 206 and plate B 208 are substantially parallel to one another, but separated by a non-conductive appendage 214. First LIF connector part 202 also includes an LIF connector housing 216, which can be electrically conductive to provide some RFI shielding.

Second LIF connector part 204 includes two electrically conductive surfaces, i.e., a beam A 218 and a beam B 220. Beam A 218 and beam B 220 can be electrically coupled to an electrical circuit (not shown) via a beam A terminal 222 and a beam B terminal 224, respectively. Beam A 218 and beam B 220 are each composed of a resilient material and at rest, they are positioned such that beam A 218 and beam B 220 form a gap 226.

During mating, an insertion force is applied to bring first LIF connector part 202 together with second LIF connector part 204, and as a result, appendage 214 is inserted into gap 226. Plate A 206 contacts beam A 218 and plate B 208 contacts beam B 220. Gap 226 is widened and as beam A 218 and beam B 220 are forced away from their positions of rest, they assert a contact pressure on plate A 206 and plate B 208, respectively.

The present invention calls for a multi-row, plate-on-beam connector, having up to 500 contacts with contact spacing of less than 3mm. An insertion force ranging from 20 to 100 grams/contact is required to effectuate mating. It should be understood that various alternative low insertion force connectors concepts can be used without departing from the invention.

Figure 6A:
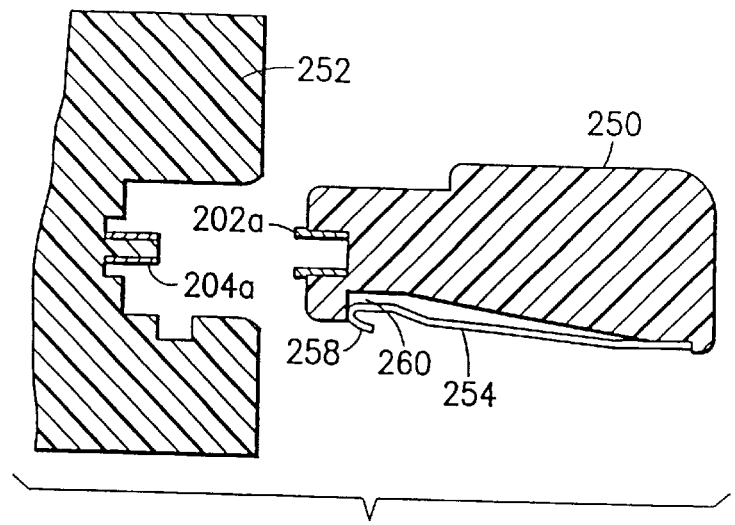
FIGS. 6a–6c are several side profile views of a new ultrasound transducer connector assembly as it is being inserted into a mating receptacle.
Figure 6B:
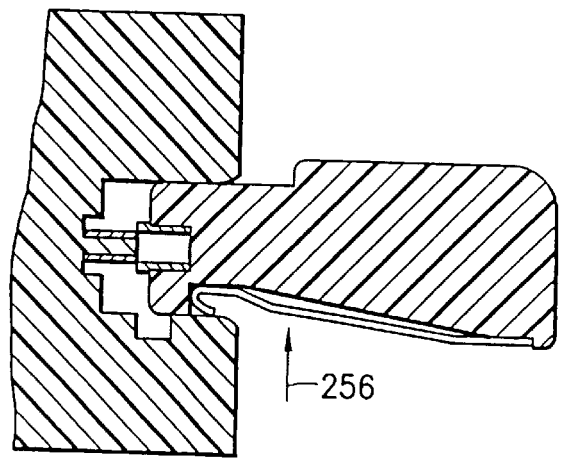
Figure 6C:
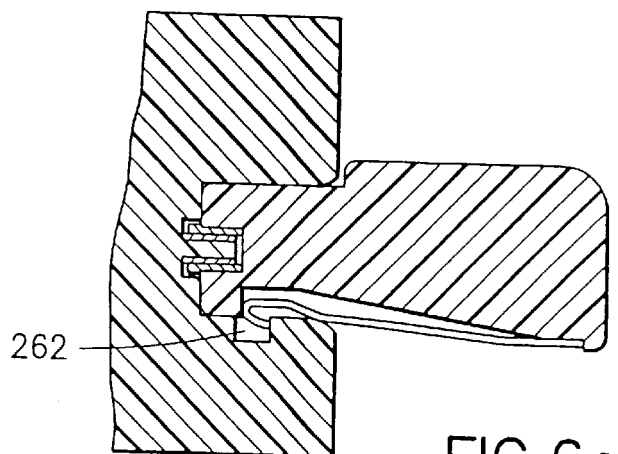
Figure 7C:
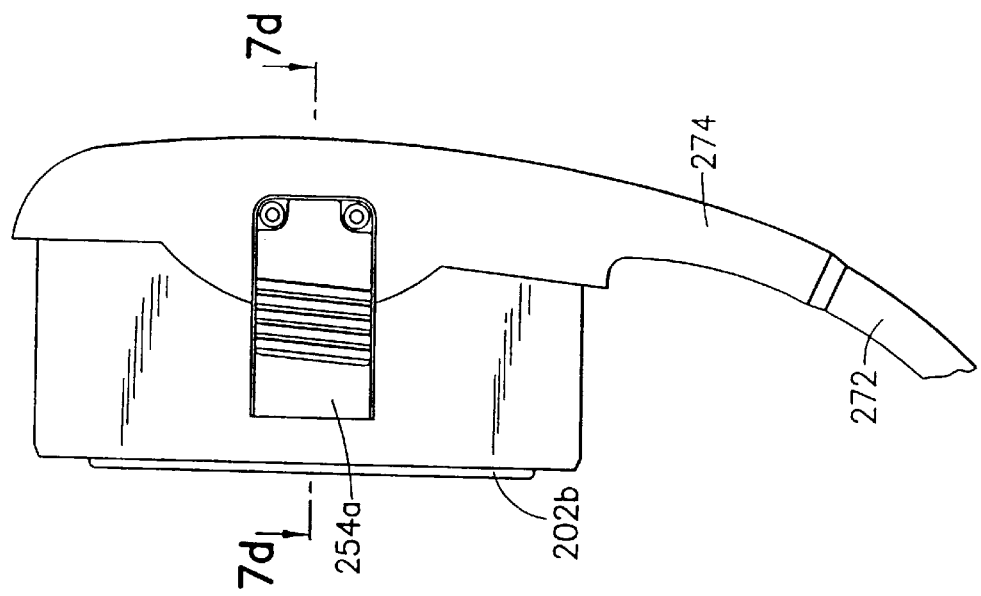
FIGS. 7a–7d are several views of a new ultrasound transducer connector assembly including a first LIF connector part of a 120-contact, multi-row plate-on-beam connector, and a leaf spring latch.
Figure 7B:
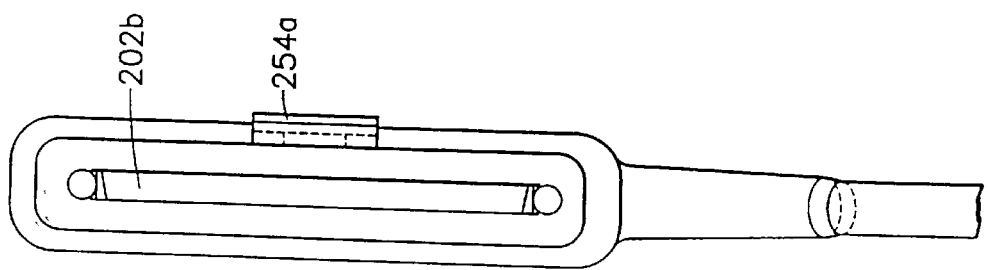
Figure 7A:
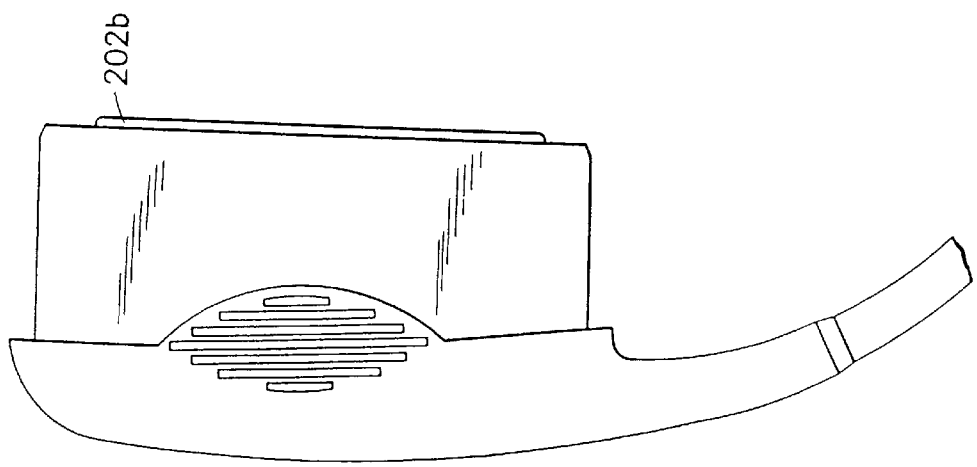

FIGS. 6a–6c show a side profile view of a new ultrasound transducer connector assembly 250 as it is being inserted into a mating terminal 252. A plate-on-beam connector having a first LIF connector part 202a will mate with a corresponding second LIF connector part 204a. Although new ultrasound transducer connector assembly 250 is shown here to include first LIF connector part 202a, the design is not limited to this configuration, and new ultrasound transducer connector assembly 250 may instead include second connector LIF connector part 204a.

Note the inclusion of leaf spring latch 254. A latch is incuded to prevent ultrasound transducer connector assembly 250 form accidentally disconnecting from mating terminal 252. FIGS. 6a and 6b show that during insertion of ultrasound transducer connector assembly 250 into mating terminal 252, an applied force 256 causes a latching head 258 (also referred to as a protrusion) to retreat into a recess 260. In FIG. 6c, when ultrasound transducer connector assembly 250 is fully inserted, latching head 258 locks into recess 262. Although other latching means can be used, leaf spring latch 254 requires minimal space and is relatively inexpensive as compared to other latching devices.

FIGS. 7a–7d illustrate an example of a new ultrasound transducer connector assembly including a first LIF connector part 202b of a 120-contact, multi-row plate-on-beam connector, and a leaf spring latch 254a as previously described.

First LIF connector part 202b is coupled to an electrical circuit 270, and a cable 272 couples electrical signals from electrical circuit 270 to an ultrasound transducer (not shown). Cable strain relief 274 is included to reduce mechanical stress on cable 272 near the area where it is coupled to electrical circuit 270. Electrical circuit 270 is typically a printed circuit board populated with electrical components, but the present invention does not contemplate limiting electrical circuit 270 to any specific physical configuration.

The regions designated by reference numbers 280, 282 and 284 collectively represent a connector housing. The new ultrasound transducer connector assembly can employ one of three housing configurations. These housing configurations are described below.

Figure 8:
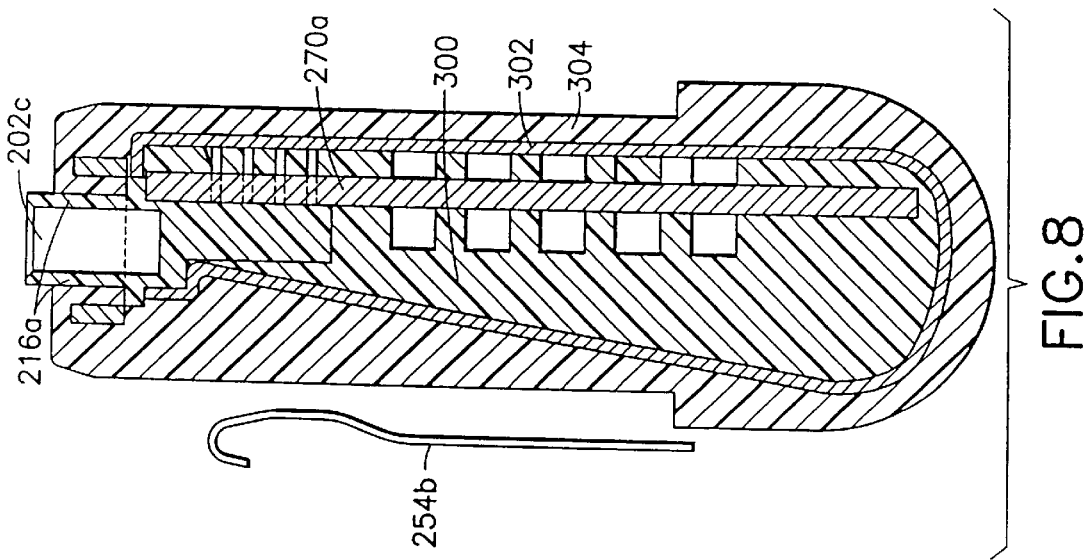
FIG. 8 is a cross-sectional view of a new ultrasound transducer connector assembly employing a first housing configuration.
Figure 7D:
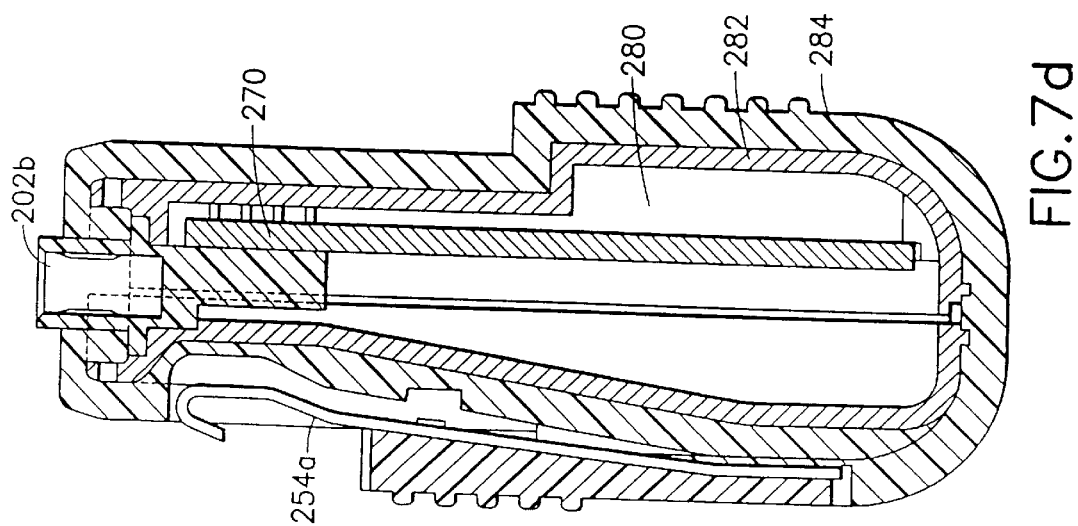

FIG. 8 is a cross-sectional view of a new ultrasound transducer connector assembly employing housing configuration #1, which uses a premolding 300, an RFI shield 302 and an overmolding 304. As previously described, the assembly includes a first LIF connector part 202c with an electrically conductive LIF connector housing 216a, a leaf spring latch 254b and an electrical circuit 270a.

Premolding 300 is disposed about electrical circuit 270a. Premolding 300 is composed of a non-conductive plastic such as polyethylene, thermoplastic, thermosetting or epoxy. Polyethylene is the preferred material because it is the easiest to use and is the least expensive. It may be applied with a thickness ranging from 0.030 to 0.300 inches, preferably in the range of 0.040 to 0.080 inches.

RFI shield 302 encloses premolding 300, and is coupled to LIF connector housing 216a. RFI shield 302 can be composed of metal tape, metal wire mesh or sheetmetal.

Overmolding 304 is applied over RFI shield 302 and optionally, a portion of LIF connector housing 216a. Overmolding 304 is composed of a plastic, preferably polyvinyl chloride (PVC). It may be applied with a thickness ranging from 0.030 to 0.300 inches, preferably from 0.040 to 0.100 inches.

The successful yield of the overmolding process is about 95%. That is, about 5% of the overmolded connector assemblies are rejected due to overmolding defects. Overmolding defects cannot be repaired. Additionally, the premolding prevents access to, and repair of, the electric circuit. Accordingly, housing configuration #1 is most economically practical when the combined cost of the electric circuitry and the cable are not significantly greater than the savings afforded by using the premolding and the overmolding.

FIG. 9 is a cross-sectional view of a new ultrasound transducer connector assembly employing housing configuration #2, which uses an inner shell 320 and an overmolding 322. As previously described, the assembly includes a first LIF connector part 202d with an electrically conductive LIF connector housing 216b, a leaf spring latch 254c and an electrical circuit 270b.

Inner shell 320 encloses electrical circuit 270b, and is coupled to LIF connector housing 216b. Inner shell 320 is composed of either a conductive metal or a metalized plastic. Metalized plastic is a plastic, such as thermoplastic or thermosetting, coated with a metal film. The metal film is electrically conductive and can be applied with a thickness ranging from 0.00001 to 0.010 inches, preferably from 0.0001 to 0.001 inches. As inner shell 320 is conductive, it also serves as an RFI shield.

Overmolding 322 is applied over inner shell 320, and optionally, a portion of LIF connector housing 216b. Overmolding 322 is composed of a plastic, preferably polyvinyl chloride (PVC). It may be applied with a thickness ranging from 0.030 to 0.300 inches, preferably from 0.040 to 0.100 inches.

If an overmolding defect occurs, overmolding 304 and inner shell 302 can be removed, and electrical circuit 270a can be salvaged and reworked. However, during the overmolding process, if the perimeter of inner shell 304 has any gap, the overmolding plastic may leak into the interior region 324 and damage electrical circuit 270a.

FIG. 10 is a cross-sectional view of a new ultrasound transducer connector assembly employing housing configuration #3, which uses an inner shell 340, a conductive wrap 342, and an outer shell 344. As previously described, the assembly includes a first LIF connector part 202e with an electrically conductive LIF connector housing 216c, a leaf spring latch 254d and an electrical circuit 270c.

Inner shell 340 encloses electrical circuit 270c. Inner shell 340 is non-conductive and composed of a plastic such as thermoplastic or thermosetting.

Conductive wrap 342 encloses inner shell 340, and is coupled to LIF connector housing 216c. Conductive wrap 342 is composed of a conductive material such as copper foil or wire mesh, and it provides RFI shielding.

Outer shell 344 encloses conductive wrap 342, and optionally, a portion of LIF connector housing 216c. Outer shell 344 is preferably composed of plastic.

If electrical circuit 270c needs to be accessed or reworked, then outer shell 344, conductive wrap 342 and inner shell 340 can be removed.

Figure 11:
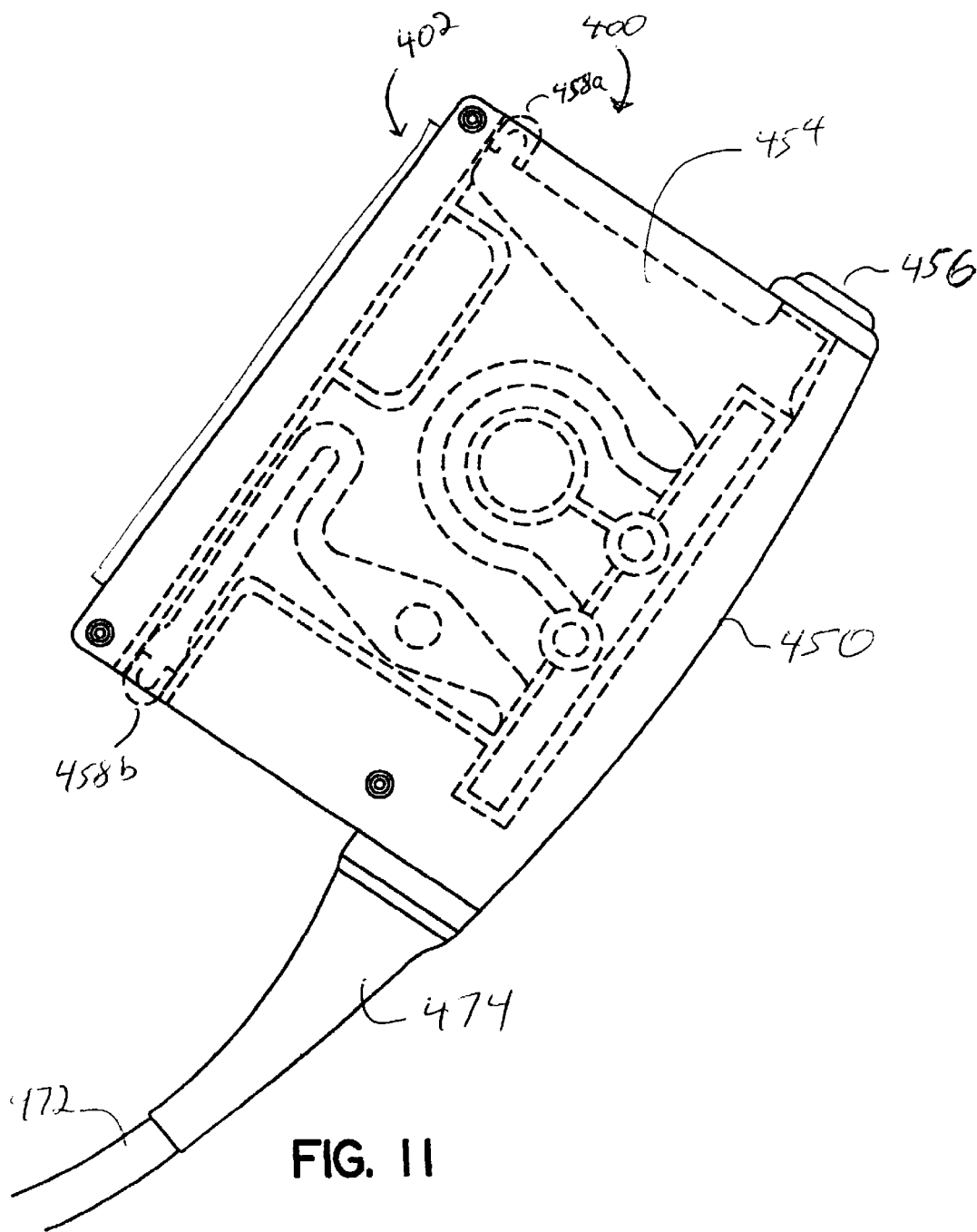
FIG. 11 is a plan view of a new ultrasound transducer connector assembly in accordance with a preferred embodiment of the present invention.

FIG. 11 is a plan view of a new ultrasound transducer connector assembly 400 in accordance with a preferred embodiment of the present invention. As with the previous preferred embodiments, the connector assembly 400 utilizes a LIF connector 402 by an shell 450. The shell 450 also secures a cable strain relief 474 which reduce mechanical stress on a cable 472 near the area where it is coupled to an electrical circuit (not shown) that electrically connects the LIF connector 402 to the leads in the cable 472. A latch mechanism 454 is also secured by the shell 450. The latch mechanism 454 is actuated by a button 456, movably secured by the outer shell 450, and upon such actuation retracts protrusions 458a and 458b. Protrusion 548a and 458b engage concave depressions in a mating terminal(not shown).

Figure 12:
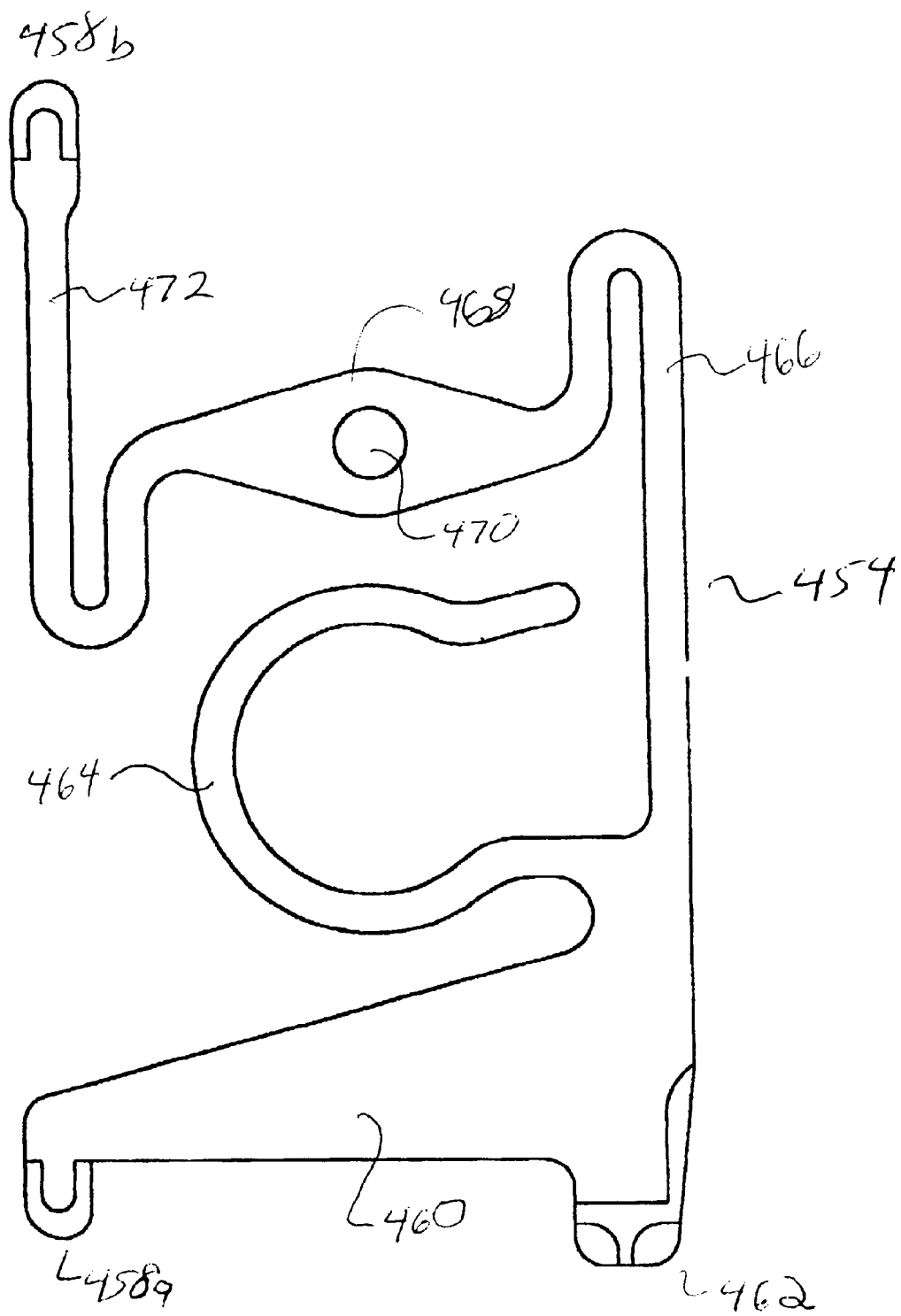
FIG. 12 is a plan view of a latch mechanism as used in the new ultrasound transducer connector assembly shown in FIG. 11.

FIG. 12 is a plan view of the latch mechanism 454 as used in the new ultrasound transducer connector assembly 400 shown in FIG. 11. The latch mechanism 454 generally functions to extend and retract the first protrusion 458a and the second protrusion 458b. When at rest, the latch mechanism biases the protrusions 458a and 458b in opposite directions, outward. When the button 456 (see FIG. 11) is pressed, the latching mechanism 454 retracts the protrusions 481 and 458b by retracting them toward the inside of the outer shell 450 (see FIG. 11). The latch mechanism 454 is preferably formed of delrin 500T.

A first rigid area 460 mechanically connects a button interface 462 with the first protrusion 458a, such that when the button 456 is pressed the protrusion 458a moves in the same direction as the button 456 against a biasing force provided by a spring portion 464. The spring portion 464 is secured by suitable inward facing projection on the outer shell 450. An actuator rod 466 mechanically links the button interface 462 with the second protrusion 458b. When the button 456 is pressed, the actuator rod 466 is forced coaxially in the same direction as the movement of the button 456 (against the biasing force of the spring portion 464). A first end of a pivot portion 468, connected to an end of the actuator rod 466 opposite that of the button interface 462, translates the motion of the actuator rod 466 into a direction opposite that of the movement of the button 460 by pivoting about a pivot point, for example point 470. A second end of the pivot portion 468 is connected to a second actuator rod 472 that couples the reverse motion of the pivot portion 468 to the second protrusion 458b.

Figure 13:
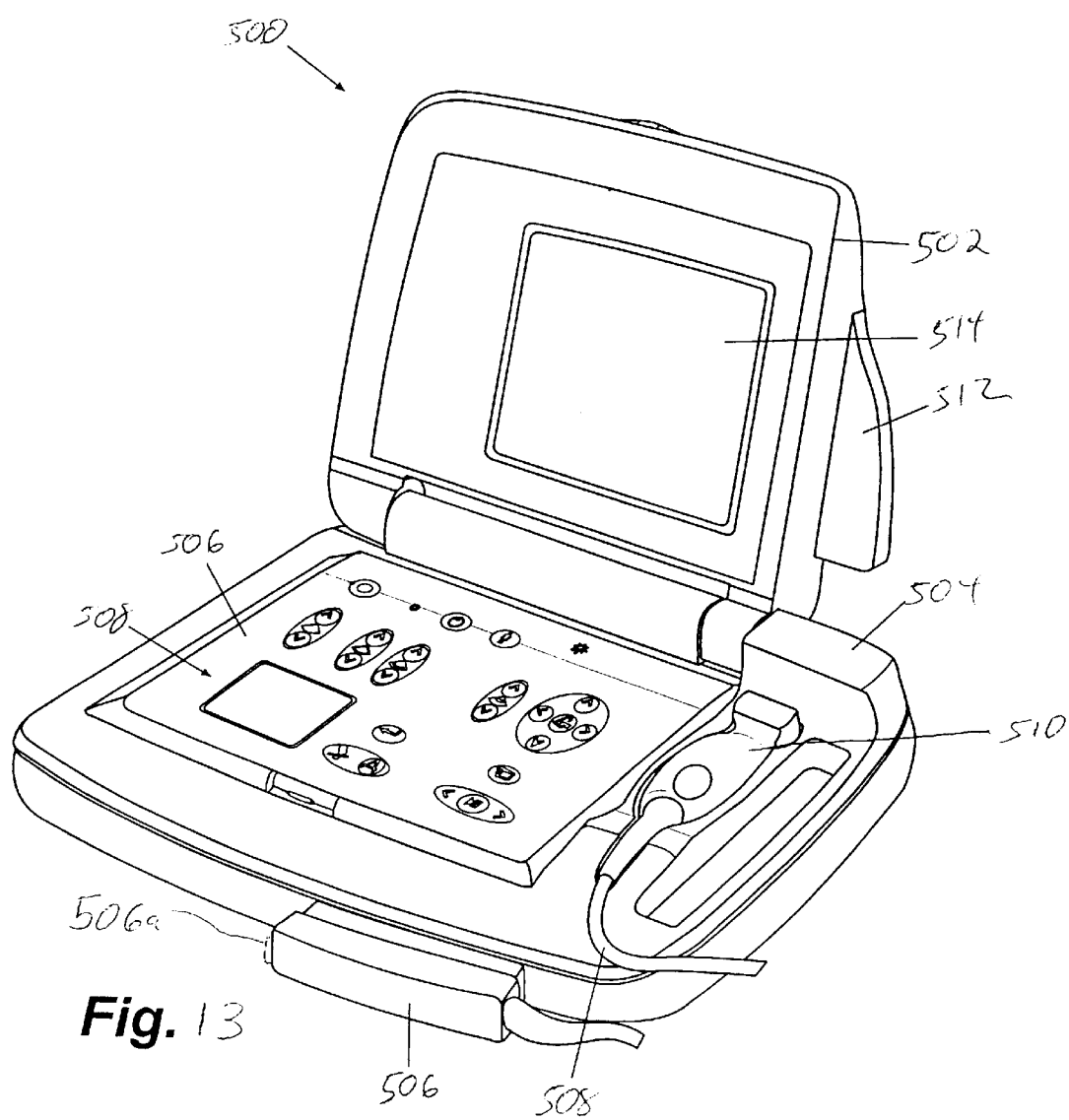
FIG. 13 is a perspective view of a portable ultrasound device including an ultrasound connector assembly in accordance with the present invention.

FIG. 13 is a perspective view of a portable ultrasound device 500 including an ultrasound connector assembly in accordance with the present invention. The ultrasound diagnostic device 500 of the present invention preferably is 13½ inches long, 9.5 inches wide and 3.5 inches thick, although those skilled in the art will understand that the present invention is not limited to these exact dimensions. The weight of the device 500 preferably is less than 7.7 pounds, including the control circuitry, the battery pack, the carrying strap and the transducer assembly, which are all discussed below in detail. The manner in which this lightweight design has been achieved in accordance with the invention is attributable to the overall design and construction of the device 500 and to the judicious selection of electrical and data storage components implemented in the device 500 including the incorporation of the subject matter of the present invention: the transducer connector. As noted above, the use of a LIF connector insert enables the use of a single PCB in the connector and reduces the size and weight of the connector.

The device 500 is similar in design to a laptop computer, except that it is smaller than many typical laptop computers. The device 500 comprises a display portion 502 and a console portion 504. To open the device 500, the user opens the display portion 502 by unlatching and lifting up on the display portion 502 at a location near a front end of the device 500. The display portion 502 is in a hinging relationship with the console portion 504 so that when the user lifts up on display portion 502, the display portion 502 is rotated upwards (i.e., away from the console portion 504). The hinging relationship is provided by a hinging mechanism which couples the display portion 502 to the console portion 504 at one or more locations adjacent a rear surface of the ultrasound diagnostic device 500. The hinging mechanism may be similar to hinging mechanisms typically used with laptop computers currently available on the market.

The display portion 502 include a display screen 514, typically comprising a full-color liquid crystal display (LCD) screen, or other type of full color display. Preferably, the display screen 514 is large enough to provide a high quality image and is small enough to maximize the portability of the ultrasound diagnostic device 500. The console portion 504 comprises a small control panel 516 having a number of keys 508. Each of the keys 508 includes an icon that is descriptive of the key's functionality.

A transducer assembly is removably connected by a connector 506 to the ultrasound diagnostic device 500 and comprises the connector 506, a transducer cable 508, and a transducer 510. The connector 506 may be of any configuration discussed herein above but preferably is configured as shown in FIG. 11 with a button 506*a*. To facilitate integration with the portable ultrasound diagnostic device 500, the connector 506 should at least have the following features: a non-ZIF connector (preferably a LIF connector) that is secured to the console portion with a latch mechanism (not shown) which engages a mating mechanism (not shown) in a terminal (not shown) formed in the console portion 504. Preferably, the engagement of the mating mechanism is based on a linear, or near linear, movement of imparted by the user as opposed to the twist mechanisms of the prior art. Preferably, the transducer 510 is small enough to fit comfortably in the palm of the hand of the user so that a user can easily manipulate it.

The connector 506 not only enables different types of transducer assemblies to be implemented with the ultrasound diagnostic device 500 but also maintains the diminutive dimensions of the device 500 while providing adequate security against the connector 506 inappropriately disengaging from the console portion 504. By forgoing the traditional twist lock, the present invention also present a smooth exterior that should not catch on obstructions. Depending on the bodily feature being imaged, different transducer assemblies can be utilized with the ultrasound diagnostic device 500. The user can easily (when compared with prior art devices) unplug one type of transducer assembly and easily plug another transducer assembly into the terminal. Of course, each transducer assembly must be adapted to mate with the receptacle. This provides the ultrasound diagnostic device 500 with great flexibility with respect to its applications, as will be understood by those skilled in the art. For example, a cardiologist doing rounds at a hospital may use the ultrasound diagnostic device 500. Rather than using a stethoscope to check patients' heart beats, the cardiologist may connect the appropriate transducer assembly to the device 500 and use the device 500 in the same manner in which a conventional stethoscope is used. In contrast, a gynecologist may use the ultrasound diagnostic device to perform fetal monitoring. In this case, a transducer assembly, which is suitable for this purpose, will be plugged into the receptacle.

The transducer 510 is designed to fit within a recess in the console portion 504 and is covered by an extended portion 512 of the display portion 502 when the display portion 502 is closed over the console portion 504. When the system closes, the power is turned off automatically. The console portion 504 also includes an integrated handle, which includes a recess configured to provide storage of the transducer cable 508. In use, the user may, for example, set the ultrasound diagnostic device 500 on a patient's bed, rotate the display portion 502 to an appropriate viewing position, turn on the device 500, and manipulate the transducer 510 to image the patient's heart.

It should be understood that various alternatives and modifications can be devised by those skilled in the art without departing from the invention. For example, the ultrasound transducer connector shells could be composed of plastics or conductive wraps other than the types mentioned above. Accordingly, the present invention is intended to embrace all such alternatives, modifications and variances that fall within the scope of the appended claims.

What is claimed is:

1. An ultrasound transducer connector for connecting a transducer to a terminal on an ultrasound unit, the ultrasound transducer connector comprising:

a shell;

a connector supported by the shell;

a cable that electrically connects the connector to the transducer; and latching means that mechanically secures the connector to the terminal, wherein the latching means is actuated by a button to retract at least one protrusion.

2. The ultrasound transducer connector of claim 1, wherein the latching means comprises a leaf spring latch.

3. The ultrasound transducer connector of claim 1, wherein the connector is a non-ZIF connector.

4. The ultrasound transducer connector of claim 1, wherein the connector is a LIF connector.

5. The ultrasound transducer connector of claim 1, wherein the connector has a volume of less than or equal to 10 cubic inches.

6. The ultrasound transducer connector of claim 1,
wherein the connector has a weight of less than or equal to 200 grams.

7. The ultrasound transducer connector of claim 1, further comprising:

a single printed circuit board that integrates the circuits of the connector.

8. An ultrasound transducer connector for connecting a transducer to a terminal on an ultrasound unit, the ultrasound transducer connector comprising:

a shell;

a LIF connector supported by the shell;

a cable that electrically connects the LIF connector to the transducer; and a latch mechanism that mechanically translates a movement imparted by a user so as to retract at least one protrusion.

9. The ultrasound transducer connector of claim 8, wherein the latch mechanism is a leaf spring latch that biases a protrusion outward from the shell and when pressed moves the protrusion toward the shell.

10. The ultrasound transducer connector of claim 8, wherein the latch mechanism comprises:
   a least one protrusion; and
   a button that, when activated, retracts the protrusion at least part way into the shell.

11. The ultrasound transducer connector of claim 8, wherein the latch mechanism comprises:
   a button that receives a motion from a user;
   a first rigid area that mechanically connects the button to a first protrusion, such that when the button moves in a first direction, the first protrusion also moves in the first direction;
   a first actuator rod in communication with the button, such that when the button moves in the first direction, the first actuator rod is forced in the first direction;
   a pivot portion having a first end connected to the first actuator rod such that when the button is moved in the first direction a second end of the pivot portion moves in a second direction; and
   a second actuator rod connected to the second end of the pivot portion that couples the motion of the second end of the pivot portion to a second protrusion.

12. The ultrasound transducer connector of claim 8, further comprising a spring portion that biases the first protrusion in the second direction and the second protrusion in the first direction.

13. A portable ultrasound device comprising:
   a main unit including a terminal; and
   a probe assembly including:
      a transducer;
      a connector for connecting the transducer to the terminal on the main unit, the ultrasound transducer connector including:
         a shell;
         a connector supported by the shell;
         a cable that electrically connects the LIF connector to the transducer; and
         latching means for mechanically securing the electrical connector to the terminal, the latching means comprising:
            a button that receives a motion from a user;
            a first rigid area that mechanically connects the button to a first protrusion, such that when the button moves in a first direction, the first protrusion also moves in the first direction;
            a first actuator rod in communication with the button, such that when the button moves in the first direction, the first actuator rod is forced in the first direction;
            a pivot portion having a first end connected to the first actuator rod such that when the button is moved in the first direction a second end of the pivot portion moves in a second direction; and
            a second actuator rod connected to the second end of the pivot portion that couples the motion of the second end of the pivot portion to a second protrusion.

14. The ultrasound transducer connector of claim 13, wherein the latching means comprises a leaf spring latch.

15. The ultrasound transducer connector of claim 13, wherein the connector is a LIF connector.

* * * * *